US012329982B2

(12) United States Patent
Friedman et al.

(10) Patent No.: US 12,329,982 B2
(45) Date of Patent: Jun. 17, 2025

(54) USE OF COLD ATMOSPHERIC PRESSURE PLASMA TO TREAT WARTS

(71) Applicant: Drexel University, Philadelphia, PA (US)

(72) Inventors: Peter C. Friedman, New City, NY (US); Vandana Miller, Philadelphia, PA (US); Gregory Fridman, Philadelphia, PA (US); Abraham Lin, Antwerp (BE); Alexander Fridman, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 18/486,722

(22) Filed: Oct. 13, 2023

(65) Prior Publication Data

US 2024/0189613 A1    Jun. 13, 2024

Related U.S. Application Data

(63) Continuation of application No. 17/255,853, filed as application No. PCT/US2019/039170 on Jun. 26, 2019, now abandoned.

(60) Provisional application No. 62/692,126, filed on Jun. 29, 2018.

(51) Int. Cl.
*A61N 1/08* (2006.01)
*A61N 1/44* (2006.01)
*A61N 1/04* (2006.01)

(52) U.S. Cl.
CPC .............. *A61N 1/44* (2013.01); *A61N 1/08* (2013.01); *A61N 1/0468* (2013.01)

(58) Field of Classification Search
CPC .......... A61N 1/44; A61N 1/08; A61N 1/0468
See application file for complete search history.

(56) References Cited

U.S. PATENT DOCUMENTS

| | | |
|---|---|---|
| 6,629,974 B2 | 10/2003 | Penny et al. |
| 6,723,091 B2 | 4/2004 | Goble et al. |
| 2006/0009763 A1 | 1/2006 | Goble et al. |
| 2006/0084158 A1 | 4/2006 | Viol |
| 2013/0345620 A1 | 12/2013 | Zemel et al. |
| 2017/0050039 A1 | 2/2017 | Short et al. |
| 2017/0216615 A1 | 8/2017 | Pledge et al. |
| 2021/0282831 A1 | 9/2021 | Friedman et al. |

FOREIGN PATENT DOCUMENTS

| | | |
|---|---|---|
| DE | 102012103362 A1 | 10/2013 |
| RU | 2314769 C2 | 1/2008 |
| WO | 2018/026750 A1 | 2/2018 |

OTHER PUBLICATIONS

Friedman, P.C., et al., "Successful treatment of actinic keratoses using nonthermal atmospheric pressure plasma: A case series," Journal of the American Academy of Dermatology, vol. 76, No. 2, Feb. 2017, pp. 349-350.

(Continued)

*Primary Examiner* — Ankit D Tejani
*Assistant Examiner* — Joshua Brendon Solomon
(74) *Attorney, Agent, or Firm* — BakerHostetler

(57) ABSTRACT

A method for treating a wart on skin of a patient includes guiding non-thermal, atmospheric pressure plasma over areas of the tissue having the wart for a length of time effective to give rise to an at least partial amelioration of the wart.

9 Claims, 2 Drawing Sheets

Device used for wart treatment
151x111mm (96 x 96 DPI)

(56) References Cited

OTHER PUBLICATIONS

Lademann J, et al. "Risk assessment of the application of a plasma jet in dermatology," Journal of Biomedical Optics, vol. 4, No. 5, Sep.-Oct. 2009, pp. 054025-1-054025-6.
Wirtz, M., et al., "Actinic keratoses treated with cold atmospheric plasma," Journal of the European Academy of Dermatology and Venereology, vol. 32, No. 1, Jan. 2018, pp. e1-e40.
Zimmermann, J.L., et al., "Effects of cold atmospheric plasmas on adenoviruses in solution," Journal of Physics D Applied Physics, vol. 44, No. 50, Dec. 2011, pp. 505201, pp. 9.
Zucker, S.N., et al. "Preferential induction of apoptotic cell death in melanoma cells as compared with normal keratinocytes using a non-thermal plasma torch," Cancer Biology & Therapy, vol. 13, No. 13, Nov. 2012, pp. 1299-1306.

Device used for wart treatment
151x111mm (96 x 96 DPI)

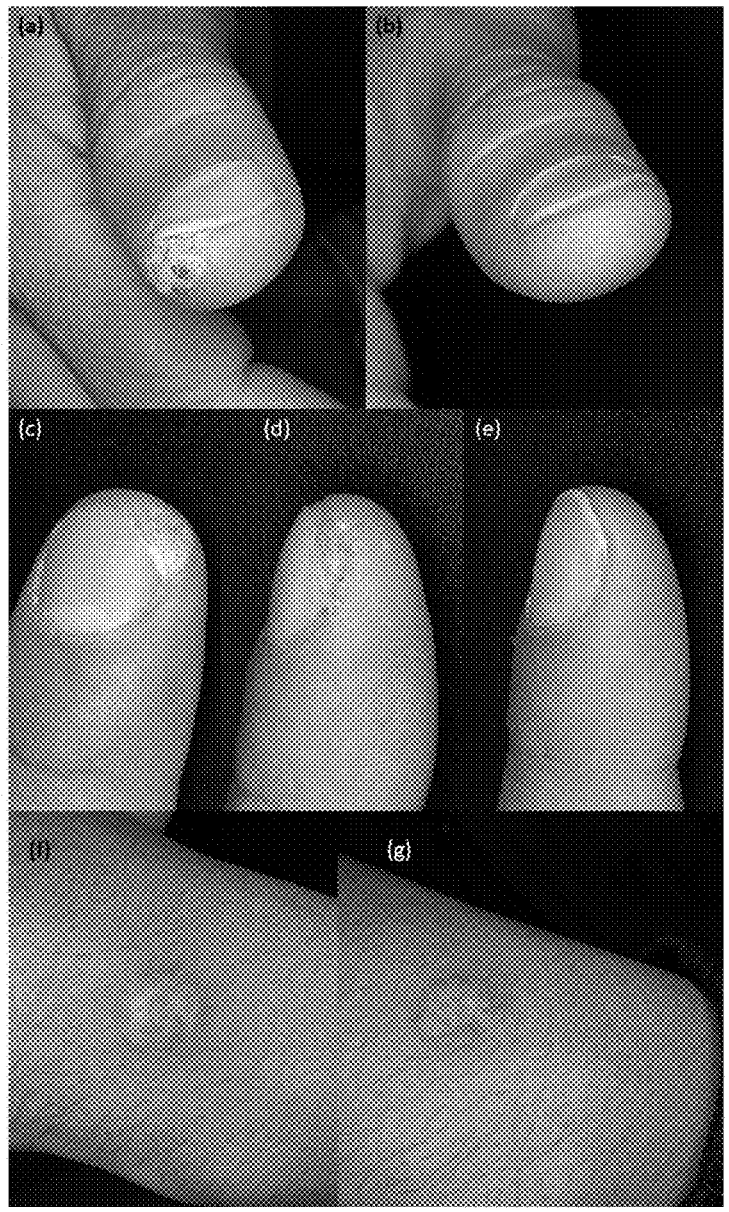
Figure 2. Warts treated with cold atmospheric pressure plasma
190x319mm (96 x 96 DPI)

USE OF COLD ATMOSPHERIC PRESSURE PLASMA TO TREAT WARTS

CROSS REFERENCE TO RELATED APPLICATIONS

This application is a continuation of U.S. patent application Ser. No. 17/255,853, filed Dec. 23, 2020; which is the National Stage of International Application Number PCT/US2019/039170, filed Jun. 26, 2019; which claims the benefit of U.S. Provisional Application No. 62/692,126, filed Jun. 29, 2018. The entireties of all foregoing applications are incorporated herein for any and all purposes.

TECHNICAL FIELD

This disclosure relates to treating skin conditions. Particularly, the disclosure relates to using plasma to treat warts and other conditions of the skin.

BACKGROUND

Skin conditions and diseases are prevalent and are often difficult to treat. If left untreated, they may progress to more serious conditions and may lead to more severe consequences, such as permanent scarring or various cancers. Skin warts, for example, are rough growths that appear on the skin. Warts can cause physical and emotional discomfort to inflicted individuals. The present invention is intended to address some of these issues.

SUMMARY

According to an aspect of the disclosure, a method for treating a wart on skin of a patient includes guiding non-thermal, atmospheric pressure plasma over areas of the tissue having the wart for a length of time effective to give rise to an at least partial amelioration of the wart.

According to another aspect of the disclosure, a device for treating a wart on skin of a patient includes a high voltage electrode, an insulating or semiconducting barrier, a power source capable of providing a voltage, and a pulse generator. The device is capable of generating non thermal plasma.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In the drawings:

FIG. 2 depicts warts treated with cold atmospheric pressure plasma, showing, in the top row: Patient 1: Partially subungual wart located on the thumb tip before the first treatment (a) and five months after the second treatment (b); showing in the middle row: Patient 1: Wart on index finger before treatment (c), two months after the first treatment (d) and four months after the third treatment (e) (Other two treated lesions of Patient 1 are not shown); showing in the bottom row: Patient 2: Wart before treatment (f) and five months after the second treatment (g). (Patient 2 was unavailable for additional treatments or interval evaluations).

Aspects of the disclosure will now be described in detail with reference to the drawings, wherein like reference numbers refer to like elements throughout, unless specified otherwise.

DETAILED DESCRIPTION OF ILLUSTRATIVE EMBODIMENTS

Figure 1:
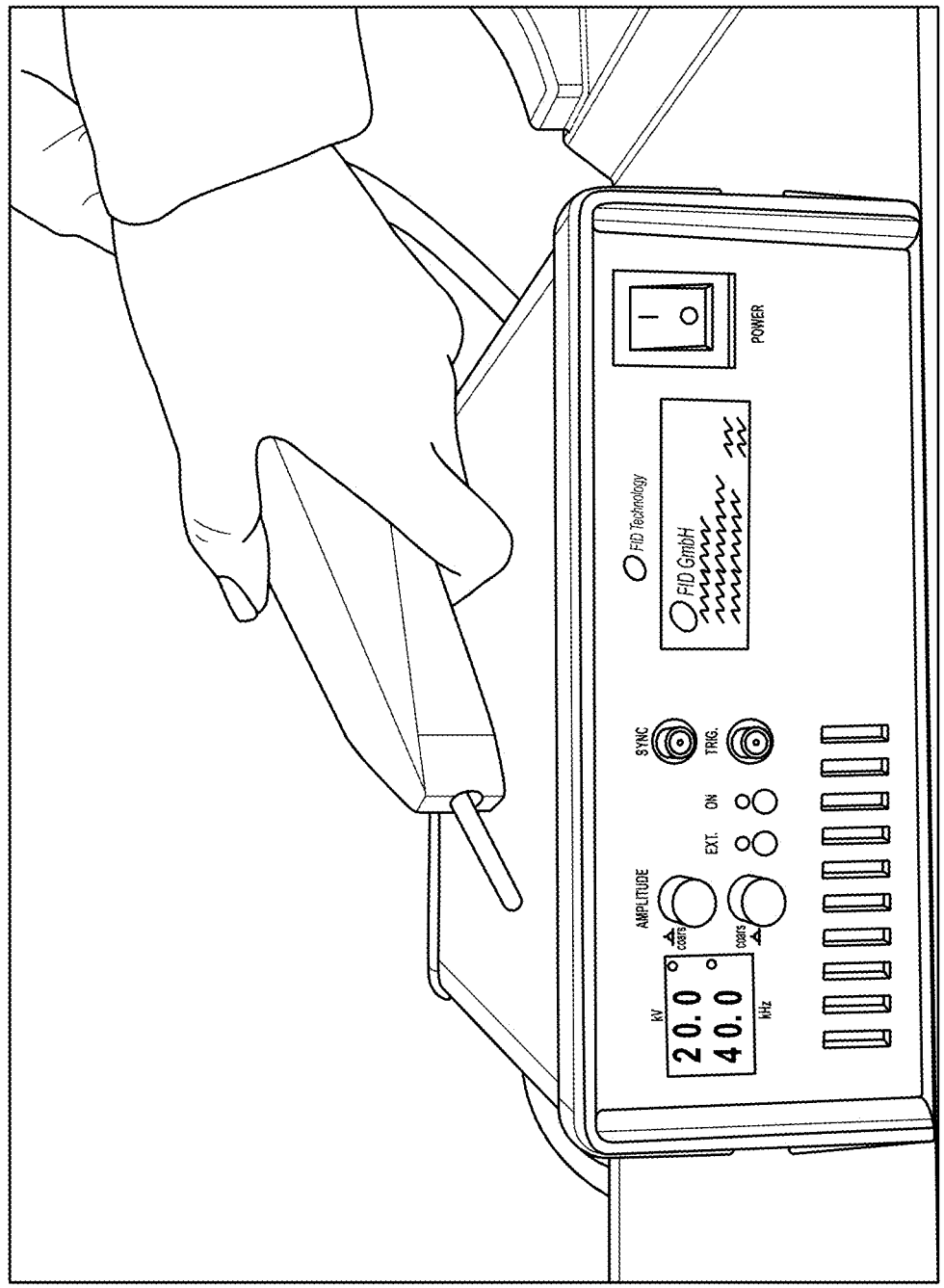
FIG. 1 depicts a device for wart treatment according to an embodiment.

Plasma is often described as the fourth state of matter. Typically, it contains charged electrons and ions as well as chemically active species such as ozone, hydroxyl radicals, nitrous oxides, electronically excited atoms and molecules. Electronic excitation of some atoms and molecules in plasma produces ultraviolet radiation (hereinafter "UV"). Plasma can also be a good electrical conductor due to the presence of charged particles in the plasma. In a room-temperature environment, plasma is usually supported by electro-magnetic fields. Light electrons absorb energy from an electric field and transfer part of this energy to heavy particles in the plasma. Plasma is considered to be thermal if the rate of the electron energy transfer is fast relative to the rate of energy losses by heavy particles. In such cases, heavy particles reach energies comparable with the energy of electrons, and the plasma becomes hot. In other cases, when electrons are not given sufficient opportunity to transfer their energy, heavier plasma components remain at much lower temperatures than the electrons. Such plasmas are called non-thermal, and their gas temperatures can be as low as room temperature.

Plasma resulting from electric discharges has been employed in the past for cauterization which primarily involves transfer of thermal energy to tissue. An example of such treatment is a treatment which uses the Argon Plasma Coagulator™ (hereinafter "APC") and related types of equipment. These devices create plasma in a flowing gas (such as argon) using a radio frequency (hereinafter "RF") electromagnetic field. Plasma in these devices plays the role of a soft electrode which is used to transfer substantial current (usually greater than 150 milli-Amperes and possibly exceeding 1 Ampere for short periods of time) into the tissue. This results in rapid heating of the tissue to over 100° C., typically causing tissue desiccation and damage.

It should be mentioned that, in more conventional electro-cautery devices, conducting electrodes made of solid materials are employed to transfer currents that heat the tissue. Tissue can stick to the solid electrodes upon heating and the use of plasma in place of a solid electrode circumvents this problem in APC, for example.

Thermal plasma devices that do not rely on delivery of current into tissue have also been developed for coagulation and cauterization of tissue. Instead, the plasma is employed to rapidly heat a gas. The heated gas (often argon due to its inert properties) is subsequently directed toward the tissue in the form of a jet whereby the heated gas transfers its thermal energy to the tissue. Examples of devices for implementation of this type of technology are the PlasmaJet™ distributed by Plasma Surgical Limited and systems patented by Rhytech Corporation (U.S. Pat. Nos. 6,629,974 and 6,723,091, and U.S. Published patent application no. US2006/0009763). The effect of such plasma treatment is mostly thermal because many of the active chemical species in the remotely created plasma are short-lived and do not survive transport of the heated gas flow to the tissue.

Thus, it is well known that electrical discharge plasma has a very strong influence on living tissue. This strong influence can be of two kinds: thermal and non-thermal. Thermal influence of plasma that results in rapid heating of living tissue is well studied and is used for, for example, cauterization. In other cases, the thermal influence of plasma results in living tissue desiccation and burns, and is thus undesirable.

The non-thermal influence of electrical discharge plasma, caused by active plasma particles (electrons, ions, radicals, and other chemically active species) and UV radiation, may be useful in many cases, for example, for living tissue disinfection and sterilization, for skin disease treatment, for blood coagulation, etc. The closer to the living tissue the active plasma is located and the higher the electrical field is in the plasma, the higher the intensity and efficacy of the non-thermal plasma treatment. Available methods of non-thermal plasma treatment are relatively weak and are effected usually by plasma jet or afterglow treatment because there are limitations on the power flux to the living tissue (to prevent overheating of the tissue) and on the total current and current density, which may flow through the living tissue (to prevent damage of the tissue and nerve channels). Since the power of electrical discharge that creates plasma is a product of the discharge current and voltage, the higher the voltage—the lower the current, when power is fixed.

Non-thermal plasmas have been developed. Non-thermal plasma discharges are used for the sterilization of equipment and various implantable plastics, for biochemical surface functionalization and treatment, and for many other applications. However, as far as the inventors are aware, non-thermal plasma technology has not been used for the various medical applications described herein, where plasma is in direct electrical contact with living tissue and acts on living tissue through various plasma-chemical processes, rather than primarily by transfer of thermal energy.

To increase efficacy of non-thermal plasma treatment and to overcome existing limitations, the present disclosure employs tissue as an electrode of a high-voltage electrical discharge with relatively low total current and current density. Under these conditions, the highest concentration of active plasma factors are located in close proximity to the treated living tissue, while the temperature of the plasma remains low because of the use of a relatively low total discharge power. In addition, total current and current density will also be low to ensure that tissue and nerve channels are not damaged.

There are many potential applications of electrical discharge plasma where the thermal effects of plasma on living tissue would be undesirable. Some of these applications include tissue disinfection and sterilization. Thermal damage to tissue during such a procedure would necessitate lengthy healing processes and use of anesthetics. Moreover, thermal damage to the surface of tissue might prevent sterilization of deeper tissue layers. Coagulation of blood without thermal tissue damage and desiccation would also help promote wound healing processes. In the absence of thermal damage, plasma could be used to promote natural processes in tissue through a combination plasma-chemical activity and UV radiation.

The high-voltage discharge generated as described in the foregoing paragraph, is similar to a Dielectric Barrier Discharge (hereinafter "DBD"), in that it may be created at standard atmospheric pressure and does not require or create high temperatures at the treatment location. For example, during DBD, the typical temperature rise is only a few degrees above room temperature.

The DBD is an alternating voltage discharge between two electrodes, at least one of which is typically covered by a dielectric. DBD plasma can be formed in the gas filled area, otherwise known as the discharge gap, between one electrode and a dielectric or between two dielectrics. The DBD is driven by an applied alternating high voltage (typically several kilovolts), which generates a high electric field between the electrodes. In the absence of a dielectric, the discharge starting from the first spark, would rapidly progress to a low-voltage arc discharge, as the electrons in the spark would initiate a series of ionization events, leading to very high current and ultimately to arc formation. The dielectric prevents arc formation by accumulating charge on the surface and generating an electric field that opposes the applied field, thereby limiting the current and preventing uncontrolled discharge development. Alternation of high voltage polarities ensures formation of this discharge in each half of the voltage cycle. Usually, DBD operates in the kilohertz range, so plasma between the electrodes does not have enough time to extinguish completely, and the discharge looks like a continuous glow and/or stationary or moving filaments in the discharge gap.

DBD is a typical discharge for non-thermal or cold plasma generation. In thermal plasmas, the temperatures of all plasma components (electrons, ions, gas molecules and atoms) are similar. Plasma can exist for some time if the plasma components are in dynamic equilibrium: recombination of electrons and ions should be balanced by ionization. To provide significant ionization, it is necessary to have energetic particles, usually electrons, with energies of several electron-volts (eV). The average energy of gas particles equals about 1 eV and corresponds to the gas temperature of 11,600 K. This means that more or less stable thermal plasmas always have temperatures above 5000 K.

In non-thermal plasmas, temperatures of components can be very different and do not have to be in equilibrium. Usually the temperature of electrons is much higher (more than 10,000 K) than the temperature of heavy particles, such as ions and gas molecules. Typically, low-temperature plasma exists in luminescent lamps. Gas temperatures of the non-equilibrium plasma can be very different and may range from room or ambient temperature to several thousand degrees Kelvin. Plasma is considered to be non-thermal when its gas temperature is not considerably higher than the surrounding temperature, which surrounding temperature may be, for example, room temperature (e.g. 20-25° C.). For the purposes of this invention, non-thermal plasma can be characterized by an average plasma gas temperature that does not exceed 100° C. The plasma electron and ion density may be about $10^{11}$ cm$^{-3}$ to about $10^{13}$ cm$^{-3}$, and, more preferably, above $10^{12}$ cm$^{-3}$. Electron density in DBD filaments, for example, may be about $10^{13}$ cm$^{-3}$ and electron temperatures can range from 10,000 to 30,000K.

It is important to stress that the temperature rise in tissue obtained by transferring heat from the surrounding matter depends not only on the temperature of the surrounding matter, but also on its volume, on the tissue volume, on the heat capacities of the tissue and the surrounding matter, on the ability of the surrounding matter and tissue to conduct heat, and on the time of contact. For this reason, when non-thermal plasma is employed, the treatment process can be controlled so that tissue temperature does not rise above 50° C.

In one apparatus according to the invention, the non-thermal plasma discharge may be generated by a high frequency oscillation of high voltage of from about 5 to about 20,000 kHz, optionally, from about 10 to about 30 kHz, using a voltage of about 2 to about 50 kV, optionally, from about 10 to about 30 kV. Whereas the DBD is created by applying a high frequency voltage between two electrodes, the non-thermal plasma discharge used in this invention occurs in a highly localized region between an insulated electrode and a second electrode. The second electrode may be a nearby object, and, in many applications of the present invention the second electrode is a human or animal body.

It is typically not necessary that the human or animal body be grounded or connected to a second electrode since the plasma discharge is controlled such that the human or animal body is typically large enough, relative to the size of the plasma discharge, to allow the charge to dissipate. However, as a precaution, or if it is desirable to employ a relatively high charge, a second electrode, ground or both, may be included in the apparatus. It is also possible to have a body connected to a second electrode connected to a power supply, or alternatively to have the body grounded to the power supply via a grounding component in order to have a closed loop, if desired.

In one embodiment of an apparatus of the present invention, a substantially completely insulated electrode 10, is energized by a high frequency, high voltage power source. No voltage is applied to the nearby object. In this embodiment, the object which may be a human or animal body, acts as a floating electrode. For this reason this non-thermal plasma discharge may be referred to as a floating electrode dielectric barrier discharge (FE-DBD).

The geometry of the non-thermal plasma discharge is controlled by the shape and size of energized electrode 10. The ability to perform treatment without directly applying a voltage to the human or animal body, and the ability to limit the discharge current to, for example, less than about 50 milli-amperes, and, optionally, to less than 1 milli-ampere, reduces the risk of harm to the surrounding tissue or the nerve system. The non-thermal plasma discharge is a high-voltage discharge. The value of the electric field near the surface of the living tissue may exceed 200 V/mm in the moments of maximal current, and, optionally, the value of the electric field near the surface of the living tissue may exceed 500 V/mm in the moments of maximal current.

The non-thermal plasma treatment may be carried out for any suitable length of time to effect the desired result without causing unacceptable tissue damage. A suitable length of treatment time may be from about 5 seconds to about 5 minutes, optionally from about 15 seconds to about 3 minutes, and, optionally, from about 30 seconds to about 1 minute. Treatments may be provided multiple times, for example 2, 3, 4, 5, 6, 7, 8, 9, or 10 times, over a period of 1, 3, 5, or more weeks. In some embodiments, the plasma may be moved along the surface of the tissue such that the plasma maintains contact with the tissue. The treatment time and frequency/number of treatment may vary depending on the properties of the specific plasma discharge employed and the apparatus employed to apply the discharge. Such variations are within the ability of skilled persons.

In some embodiments, the power source may provide power in a range of from about 5 kV to 10 kV, from 10 kV to 20 kV, from 20 kV to 30 kV, from 30 kV to 40 kV, from 40 kV to 50 kV, or in a range comprising two or more of these ranges. In preferred embodiments, the power source provides power of about 20 kV to the electrode.

In some embodiments, the pulse generator may provide a series of pulses in a range of from 50 Hz to 100 Hz, from 100 Hz to 200 Hz, from 200 Hz to 300 Hz, from 300 Hz to 400 Hz, from 400 Hz to 500 Hz, from 500 Hz to 1000 Hz, from 1000 Hz to 2000 Hz, from 2000 Hz to 3000 Hz, from 3000 Hz to 4000 Hz, or a range defined by two or more of these ranges, preferably about 400 Hz.

In some embodiments, the pulse generator may provide a series of pulses, each pulse having a duration in a range of about 10 ps to 100 ps, from 100 ps to 1 ns, from 1 ns to 5 ns, from 5 ns to 10 ns, from 10 ns to 20 ns, from 20 ns to 30 ns, from 30 ns to 40 ns, from 40 ns to 50 ns, from 50 ns to 60 ns, from 60 ns to 80 ns, from 80 ns to 100 ns, from 100 ns to 200 ns, from 200 ns to 300 ns, from 300 ns to 400 ns, from 400 ns to 500 ns, or a range defined by two or more of these ranges, preferably about 20 ns.

The need for multiple treatments, recurrences, side effects associated with treatments make treating warts frustrating for patients and dermatologists alike. Cold Atmospheric-pressure Plasma (CAP) is an ionized gas that has been extensively studied for medical applications, including clinical trials for skin conditions. Safety of CAP use on skin has been well demonstrated in the past (See, Lademann J, et al. Risk assessment of the application of a plasma jet in dermatology. J Biomed Opt 2009; 14(5):054025(1-6)).

Experimental Results

Patient 1, a 33-year-old man, presented with four warts on his fingers. He failed over the counter products and liquid nitrogen treatments performed over six months. Patient 2, a 28-year-old man, presented with a wart on the wrist. He refused cryotherapy because of possible hypopigmentation and could not afford topical medications.

Both patients were enrolled in a study approved by the Western Institutional Review Board (Nov. 10, 2016; 20130084). The CAP source used was a generator supplying 20 kV pulse of 20 ns pulse width at 400 Hz (FPG10-01NM10,FID GmbH, Germany, www.fidtechnology.com) to a 5 mm diameter, 1 mm thick quartz-covered copper electrode of 10 cm length. (FIG. 1). Treatments were two minutes long for each lesion.

The thickest (right thumb) lesion of Patient 1 cleared after two treatments, his other lesions after three treatments (FIG. 2), and remained clear seven and six months later, respectively. Four months after the start a new left thumb wart appeared, which cleared with three treatments.

Patient 2 was treated twice and—according to him but not confirmed—improved but never resolved. He never returned for subsequent treatments. By the time of his five months evaluation, the wart recurred (FIG. 2).

Two patients with altogether six warts were treated. All lesions of the first patient resolved. This patient developed a new wart during the observation period, which also cleared after three treatments. This suggests that the results were due to local CAP effect and not generalized immune response.

The single lesion of the second patient improved but recurred after stopping treatments. It is unknown if continuing treatments would have altered the outcome. This recurrence indicates that CAP did not have lasting inhibitory effect on the partially cleared wart. It is unclear if there exist previous in vivo or in vitro models to explain the effect of CAP on warts, but CAP has been shown to selectively induce apoptosis in malignant cells in vitro (See, Zucker S N, Zirnheld J, Bagati A, et al. Preferential induction of apoptotic cell death in melanoma cells as compared with normal keratinocytes using a non-thermal plasma torch. Cancer Biol Ther. 2012; 13(13): 1299-306). In vivo efficacy of CAP to treat actinic keratosis has also been reported (See, Friedman P C, Miller V, Friedman G, Lin A, Fridman A. Successful treatment of actinic keratoses using nonthermal atmospheric pressure plasma: A case series. J Am Acad Dermatol 2017; 76(2):349-350; and Wirtz M et al. Actinic keratoses treated with cold atmospheric plasma. JEADV 2018; 32:e1-e40). It can be hypothesized that CAP may also induce apoptosis in warts. It has been reported that CAP inhibits adenoviruses (See, J L Zimmermann J L, Dumler K, Shimizu T, Morfill G E, Wolf A, Boxhammer V, Schlegel J, Gansbacher B, Anton M. Effects of cold atmospheric plasmas on adenoviruses in solution. J. Phys. D: Appl. Phys. 2011; 44: 505201), possibly by altering the adenovirus capsid. It is feasible that the capsid of HPV, a similarly non-enveloped DNA virus, is also susceptible to CAP induced damage. While the mechanism of action is unclear, the number of treated lesions is very small, and larger follow up studies are needed, the clinical improvement of warts achieved by CAP treatment and the lack of recurrence of fully cleared lesions after several months in this proof of concept study is promising. Encouragingly, the cost of a market ready CAP device could be on par with current electrosurgery tools.

What is claimed:

1. A method for treating a wart on skin of a patient, the method comprising:
   with a device that comprises
   (i) a high voltage electrode insulated by an insulating or semiconducting barrier,
   (ii) a power source capable of providing a voltage,
   (iii) a pulse generator, and
   (iv) a second electrode, a ground, or both,
   applying non-thermal, atmospheric pressure plasma over an area of tissue having the wart under conditions sufficient to give rise to an at least partial reduction in size of the wart,
   the non-thermal, atmospheric pressure plasma being in direct electrical contact with the wart and the wart being exposed to the high voltage electrode insulated by an insulating or semiconducting barrier, and
   the non-thermal atmospheric plasma being generated by a high frequency oscillation of the high voltage of from about 5 to about 20,000 kHz.

2. The method of claim 1, wherein the conditions sufficient to give rise to an at least partial reduction in size of the wart is to apply the non-thermal plasma to the tissue having the wart for at least one period of time lasting between about 10 seconds and about 10 minutes.

3. The method of claim 2, wherein the non-thermal plasma is applied between 1 and 5 times.

4. The method of claim 1, wherein the non-thermal plasma is delivered with a power in a range of from about 10 kV to about 50 kV.

5. The method of claim 4, wherein the power is about 20 kV.

6. The method of claim 1, wherein the non-thermal plasma is delivered with a frequency in a range of from about 50 Hz to about 3500 Hz.

7. The method of claim 6, wherein the frequency is about 400 Hz.

8. The method of claim 1, wherein the non-thermal plasma is delivered with a pulse having a duration in a range of from about 100 ps to about 500 ns.

9. The method of claim 8, wherein the pulse duration is about 20 ns.

* * * * *